(12) United States Patent
Masotti

(10) Patent No.: US 11,452,565 B2
(45) Date of Patent: Sep. 27, 2022

(54) DEVICE FOR TREATING SKIN ULCERS

(71) Applicant: EL.EN. S.P.A., Calenzano (IT)

(72) Inventor: Leonardo Masotti, Sesto Fiorentino (IT)

(73) Assignee: EL.EN. S.P.A., Florence (IT)

( * ) Notice: Subject to any disclaimer, the term of this patent is extended or adjusted under 35 U.S.C. 154(b) by 546 days.

(21) Appl. No.: 16/333,443

(22) PCT Filed: Sep. 13, 2017

(86) PCT No.: PCT/EP2017/072971
§ 371 (c)(1),
(2) Date: Mar. 14, 2019

(87) PCT Pub. No.: WO2018/050669
PCT Pub. Date: Mar. 22, 2018

(65) Prior Publication Data
US 2019/0254745 A1    Aug. 22, 2019

(30) Foreign Application Priority Data
Sep. 15, 2016  (IT) .................. 102016000092814

(51) Int. Cl.
*A61B 18/00*    (2006.01)
*A61B 18/20*    (2006.01)
(Continued)

(52) U.S. Cl.
CPC .......... *A61B 18/203* (2013.01); *A61B 18/201* (2013.01); *A61B 2017/00057* (2013.01); *A61B 2018/00458* (2013.01); *A61B 2018/00577* (2013.01); *A61B 2018/20359* (2017.05); *A61B 2018/2283* (2013.01); *A61B 2018/2285* (2017.05)

(58) Field of Classification Search
CPC .............. A61B 18/203; A61B 18/201; A61B 2017/00057; A61B 2018/00458; A61B 2018/00577; A61B 2018/20359; A61B 2018/2283; A61B 2018/2285; A61B 2018/20553; A61B 18/20
See application file for complete search history.

(56) References Cited

U.S. PATENT DOCUMENTS 6,156,030 A * 12/2000 Neev .................. A61B 18/20
                                                             606/10
7,101,365 B1    9/2006 Sharon
(Continued)

FOREIGN PATENT DOCUMENTS

JP    2006334438 A    12/2006

OTHER PUBLICATIONS

Global report on diabetes—2016 issued by the World Health Organization.
(Continued)

*Primary Examiner* — Eugene T Wu
(74) *Attorney, Agent, or Firm* — McGlew and Tuttle, P.C.

(57) ABSTRACT

The device comprises: a laser source (7); a treatment hand-piece (13); a light guide (11) configured to convey a laser beam from the laser source to the hand-piece. The hand-piece (13) is configured to vary the inclination of the laser beam (F2) exiting from the hand-piece with respect to a longitudinal axis (A-A) of the hand-piece.

23 Claims, 6 Drawing Sheets

(51) Int. Cl.
*A61B 17/00* (2006.01)
*A61B 18/22* (2006.01)

(56) References Cited

U.S. PATENT DOCUMENTS

| | | |
|---|---|---|
| 2002/0173780 A1 | 11/2002 | Altshuler et al. |
| 2007/0213700 A1* | 9/2007 | Davison ............ A61B 18/1402 606/32 |
| 2008/0005878 A1 | 1/2008 | Starck |
| 2008/0015556 A1 | 1/2008 | Chan et al. |
| 2008/0058783 A1 | 3/2008 | Altshuler et al. |
| 2008/0172047 A1* | 7/2008 | Altshuler ............ A61B 5/441 606/9 |
| 2008/0287930 A1 | 11/2008 | Rapoport |
| 2010/0016843 A1 | 1/2010 | Bragagna et al. |
| 2012/0197357 A1 | 8/2012 | Dewey et al. |
| 2015/0327653 A1 | 11/2015 | Decaux et al. |
| 2019/0380779 A1* | 12/2019 | Negus .................. A61B 18/203 |

OTHER PUBLICATIONS

Projections of global mortality and burden of disease from 2002 to 2030, Mathers CD, Loncar D. PLoS Med, 2006, 3 (11).
National Diabetes Statistics Report, 2014 issued by the US Center for Disease Control and Prevention.
Rapporto annuale sull'attivita di ricovero ospedaliero del Ministero della Salute—Dati SDO 2014—Annual report on the hospitalization issued by the Health Minister, SDO data, 2014.
Effectiveness of interventions to enhance healing of chronic ulcers of the foot in diabetes: a systematic review—Game F.L. et al. For IWGDF, Diabetes Metab Res Rev 2016; 32 (Suppl. 1): 154-168.
Tomlinson R.E., Silva M.I.—Skeletal Blood Flow in Bone Repair and Maintenance, Bone Res. Dec. 2013; 1(4): 311-322.

* cited by examiner

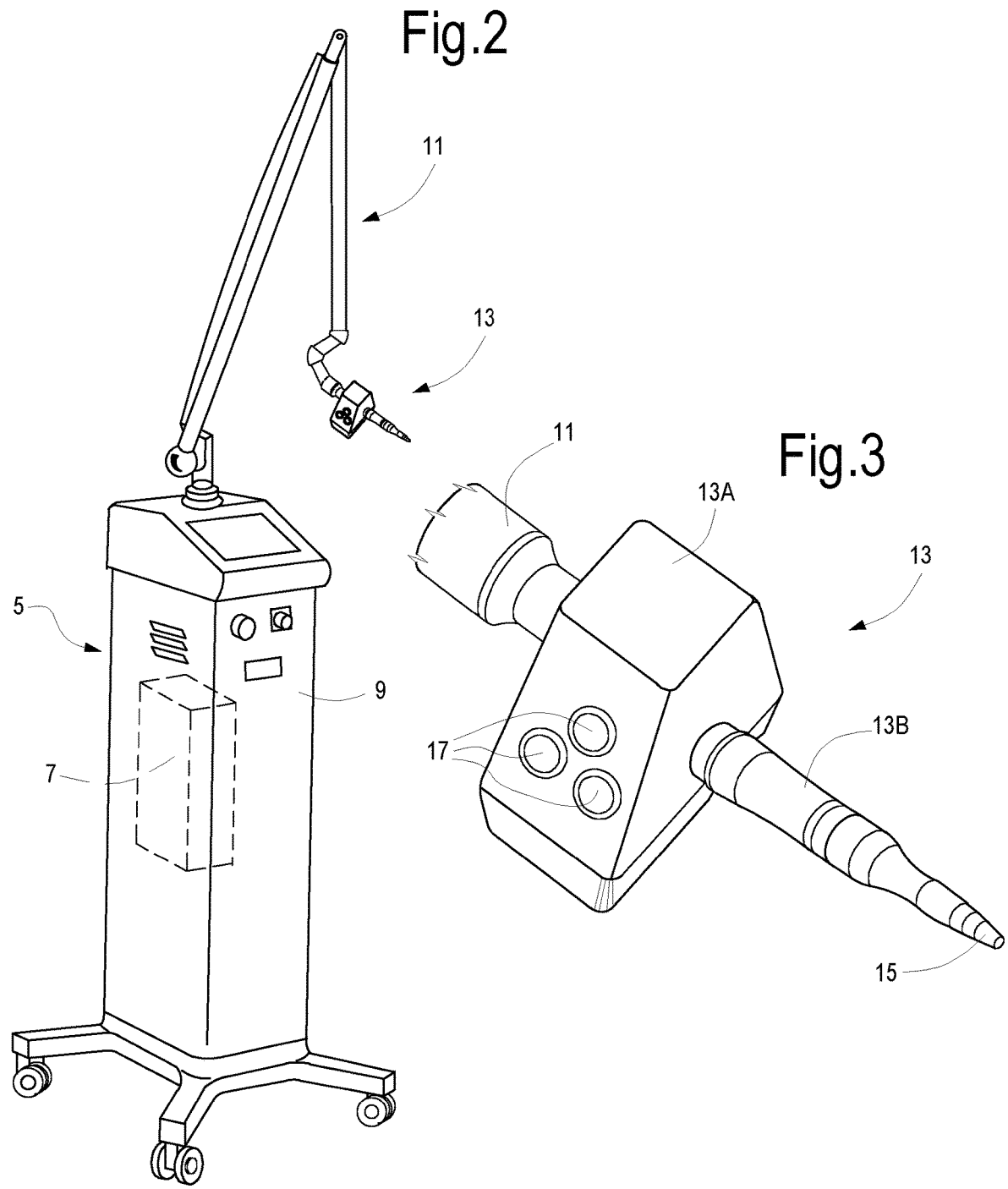

DEVICE FOR TREATING SKIN ULCERS

TECHNICAL FIELD

Devices and methods described herein concern treatment of ulcers, especially, although without limitation, diabetic ulcers.

BACKGROUND TO THE INVENTION

According to the *"Global report on diabetes—2016"* issued by the World Health Organization, in the last years diabetes has worryingly increased. The number of people suffering from diabetes is increased from 108 millions in 1980 up to 422 millions in 2014, and diabetes prevalence has risen faster in low- and middle-income countries. Diabetes is the major cause of leg amputation. Based on the trends described above, the World Health Organization forecasts that in 2030 diabetes will be the seventh cause of death in the world [*"Projections of global mortality and burden of disease from 2002 to 2030."*—Mathers C D, Loncar D. PLoS Med, 2006, 3(11)].

Amongst diabetes complications, the "diabetic foot" disease is increasingly significant; it is due to the numerous problems connected with diabetes (bad circulation, especially in legs; hyperglycemia; neuropathy). Wounds and ulcers easily form in diabetic foot; they heal slowly and hardly with the currently available medications, represent the diabetes complication with the highest number of hospitalizations, and entail very high sanitary costs. The most significant problem of diabetic foot ulcer is the high risk of amputation, especially major amputation, i.e. above the ankle. According to recent estimates, approximately 15% of people suffering from diabetes risk a foot ulcer during their life, and 85% of amputations in diabetic patients is preceded by an ulcer; diabetic foot ulcers globally represent the first cause of non-traumatic amputation of lower limbs. In 2015, the UK charity "Diabetes UK" asked the UK Government and National Health System greater engagement and higher investments for the prevention and treatment of diabetes complications, as the average number of amputations in a week, due to diabetes complications, was increased up to 135. According to the *"National Diabetes Statistics Report, 2014"* issued by the US Center for Disease Control and Prevention (CDC), in 2010 there were approximately 73,000 non-traumatic lower extremity amputations (200/day) correlated with diabetes in patients over 20 years old. In 2014 in Italy, for the DRG-Diagnosis Related Group 285C, *"Amputazioni di arto inferiore per malattie endocrine, nutrizionali o metaboliche"* (Amputations of lower limb due to endocrine, nutritional and metabolic diseases), 859 discharges and a total of 10,350 inpatient days have been recorded (Rapporto annuale sull'attività di ricovero ospedaliero del Ministero della Salute-Dati SDO 2014—Annual report on the hospitalization issued by the Health Minister, SDO data, 2014).

The economic and social impact of this problem led to the foundation, in 1996, of the International Working Group on the Diabetic Foot (IWGDF), a foundation made up by working groups of independent experts from 100 countries, producing quadrennial Practical, Specific and Consensus guidelines on the management and prevention of the diabetic foot. The IWGDF guidelines always highlight the importance of an interdisciplinary approach, strongly oriented to the prevention of diabetes in general and, in particular, of the foot ulcers, as the currently available clinical treatments are poorly effective for healing diabetic foot ulcers [*"Effectiveness of interventions to enhance healing of chronic ulcers of the foot in diabetes: a systematic review"*—Game F. L. et al. For IWGDF, Diabetes Metab Res Rev 2016; 32 (Suppl. 1): 154-168].

Therefore, in order to reduce the number of amputations it is necessary, in addition to increasing implementation of best practices in managing and preventing diabetic foot, also to improve the ability of effectively treating diabetic foot ulcer through innovative and effective technologies and therapeutic protocols.

A need therefore exists for new and more effective devices and methods for treating ulcers, especially diabetic ulcers, aimed at reducing the number of amputations and to limit patient's discomfort.

Similar problems and needs may also arise from skin ulcers of different origin, such as dehiscences, venous ulcers, arterial ulcers, decubitus ulcers or pressure ulcers.

SUMMARY OF THE INVENTION

A device for the laser treatment of skin ulcers is disclosed, comprising: a laser source; a treatment hand-piece; a light guide configured to convey a laser beam from the laser source to the hand-piece; a collimation lens, configured to collimate the laser beam coming from the source and to obtain a collimated laser beam at the exit of the hand-piece; and wherein the hand-piece is configured to vary the inclination of the laser beam exiting from the hand-piece with respect to a longitudinal axis of the hand-piece. Further features and embodiments of the hand-piece are described in the description below and in the attached clauses.

According to a further aspect, innovative methods are disclosed herein for treating ulcers such as, but without limitation, diabetic ulcers, the methods allowing to overcome, partially or completely, the problems of the currently known methods.

Essentially, according to an embodiment, a method is provided comprising a preliminary step of cleaning the ulcer, the so-called debridement or escharotomy, for eliminating necrotic infected tissue, in the most complex cases till the underlying bone tissue is exposed. Once the ulcer bed has been cleaned, using a laser beam a plurality of holes are made in the soft tissues and/or in the exposed bone tissue present in the area of the cleaned ulcer. The depth of the holes made in the exposed bone tissue is sufficient to cause blood to exit from the inside of the bone. The holes made in the soft tissues cause localized damages, i.e. micro-traumas stimulating reconstruction processes, as detailed below. The holes in the soft tissues may be made in subcutaneous tissues, i.e. tissues below the epidermis, and/or along the skin. In particular, the holes in soft tissues may be made along the edges of the wound or ulcer, as well as in the ulcer inner areas.

The cleaning step is preferably performed using a laser in order to achieve better results also as regards sterilization, and greater acceptability by the patient. However, also traditional methods can be used for cleaning the ulcer, for example ultrasounds and/or surgical cutting and erasing instruments.

The micro-trauma resulting from the holes facilitates the recovery of a series of physiological repair mechanisms, as well as a better blood flow [Tomlinson R. E., Silva M. J.—Skeletal Blood Flow in Bone Repair and Maintenance, Bone Res. 2013 December; 1(4): 311-322]. It has been surprisingly found that stem cells, especially mesenchymal stem cells, a high amount of which is in the blood contained in the bone tissue and is made available through the holes, promote efficient and fast tissue regeneration, with gradual healing and closing of the ulcer. In the blood flowing from the bone tissue through the holes made by means of laser, in addition to pluripotent stem cells also other substances are present, which facilitate and promote tissue regeneration. Specifically, the outflowing blood contains a high amount of growth factors, coagulation factors, inflammatory factors or pro-inflammatory transcription factors (such as PDGF, TGF-β IGF, VEGF, EGF).

Mesenchymal stem cells are pluripotent cells able to differentiate, both in vivo and in vitro, into osteoblasts, chondrocytes, myocytes, and many other cell types.

Tests on patients suffering from diabetic foot proved that the described method facilitates and promotes reconstruction of the bone tissue when partially attacked by the generative process as well as of soft tissues in the ulcer area, leading to a gradual joining of the ulcer edges and to the healing thereof. Stem cells exiting from the bone tissue, achieving the surface thereof and entering into contact with the surrounding soft tissues, differentiate into specialized cells, forming osteocytes and soft tissue cells.

According to preferred embodiments of the method described herein, in order to improve and accelerate the tissue regeneration process, the laser beam may be used also to make holes in the soft tissues remained in the ulcer bed after debridement. These holes represent targeted damages to the sound soft tissue remained after cleaning. The damages caused by the laser trigger off a reaction mechanism in the treated organism aimed at damage repair. This reaction mechanism causes the transmission of proteins with biological messages triggering off the tissue regeneration process. This reaction mechanism has a synergistic effect with the release of stem cells and growth factors inside the bone tissue resulted from the perforation thereof, with a consequent acceleration of the tissue regenerative process.

The formation of holes in soft tissues by means of the laser is simultaneous with the cauterization of blood vessels in these tissues, thus preventing bleeding. The hyperemia generated in the tissues causes, in turn, increased blood supply to tissue portions near the holes made by the laser beam, and this accelerates the healing process also due to the reaction mechanism mentioned above.

It has been also found that the laser radiation stimulates the regenerative process thanks not only to the cited thermal and hyperemia effect on tissues, but also to the bio-stimulation of the treated tissues by means of the laser radiation. Bio-stimulation promotes and facilitates the healing process, accelerating the multiplication of healthy cells.

In many cases ulcers, especially diabetic ulcers, also affect tendons that, attacked by necrosis, shall be partially or completely removed. Surprisingly, the method described above showed that the stem cells, extracted through bleeding caused by the holes made in the bone tissue, specialize also forming tendon cells that, analogously to the cells of the surrounding soft tissues and, in case, of osteocytes, multiply also thanks to the bio-stimulating effect and the hyperaemia effect of the laser beam.

During the treatment of diabetic ulcers or the like, the laser application can be repeated over time. For example, in a first step escharotomy or debridement of ulcer may be performed to remove the necrotic tissue and sterilize the ulcer bed. Then, a first series of holes is made in the bone tissue, if exposed, and a first series of holes is made in the cleaned soft tissues, for the purposes indicated above. After approximately one week, it is possible to verify the trend of the tissue regeneration process, and, if necessary, clean the ulcer again, and then make new holes in the bone tissue and/or the soft tissue. By proceeding in this way, with one or more laser treatments it is possible to achieve a fast healing, with the ulcer edges joining together up to the complete closing of the wound.

The ulcer can be theoretically cleaned by means of traditional methods. These methods provide, in general, for the use of scalpels or other invasive tools, entering into contact with the ulcer. In some cases, the use of ultrasounds has been suggested, by means of a suitable probe (sonotrode) also entering into physical contact with the patient. These cleaning techniques entail considerable discomfort for the patient.

Vice versa, according to some embodiments of the method described herein, ulcer debridement or escharotomy may be advantageously made by means of the laser beam. In this way, the necrotic tissues and/or of other debris in the treated area are removed without mechanical contact between tool and tissues, and therefore without pressure and curettage. This reduces pain, with better quality of life, greater tolerability of treatment, and therefore greater acceptability by the patient.

During this step, the laser beam parameters are adjusted as to cause cut and/or vaporization of tissues. The high temperatures achieved by the tissues in the laser ablation area not only ensure lower pain during the treatment, and therefore greater acceptability with respect to the traditional methods carried out with invasive tools (scalpels, sonotrodes or the like), but ensures also automatic disinfection; consequently, the ulcer bed is sterile or has a very low bacterial content.

BRIEF DESCRIPTION OF THE DRAWING

The invention will be better understood by following the description and the accompanying drawing, which shows non-limiting practical embodiments of the invention. More particularly, in the drawing:

FIG. 2 schematically shows equipment comprising the laser source of the workplace of FIG. 1;

FIG. 3 shows an enlargement of the hand-piece of the equipment of FIG. 2;

DETAILED DESCRIPTION OF EMBODIMENTS

The following detailed description of the exemplary embodiments refers to the accompanying drawings. The same reference numbers in different drawings identify the same or similar elements. Additionally, the drawings are not necessarily drawn to scale. Also, the following detailed description does not limit the invention. Instead, the scope of the invention is defined by the appended clauses.

Reference throughout the specification to "one embodiment" or "an embodiment" or "some embodiments" means that the particular feature, structure or characteristic described in connection with an embodiment is included in at least one embodiment of the subject matter disclosed. Thus, the appearance of the phrase "in one embodiment" or "in an embodiment" or "in some embodiments" in various places throughout the specification is not necessarily referring to the same embodiment(s). Further, the particular features, structures or characteristics may be combined in any suitable manner in one or more embodiments.

Figure 1:
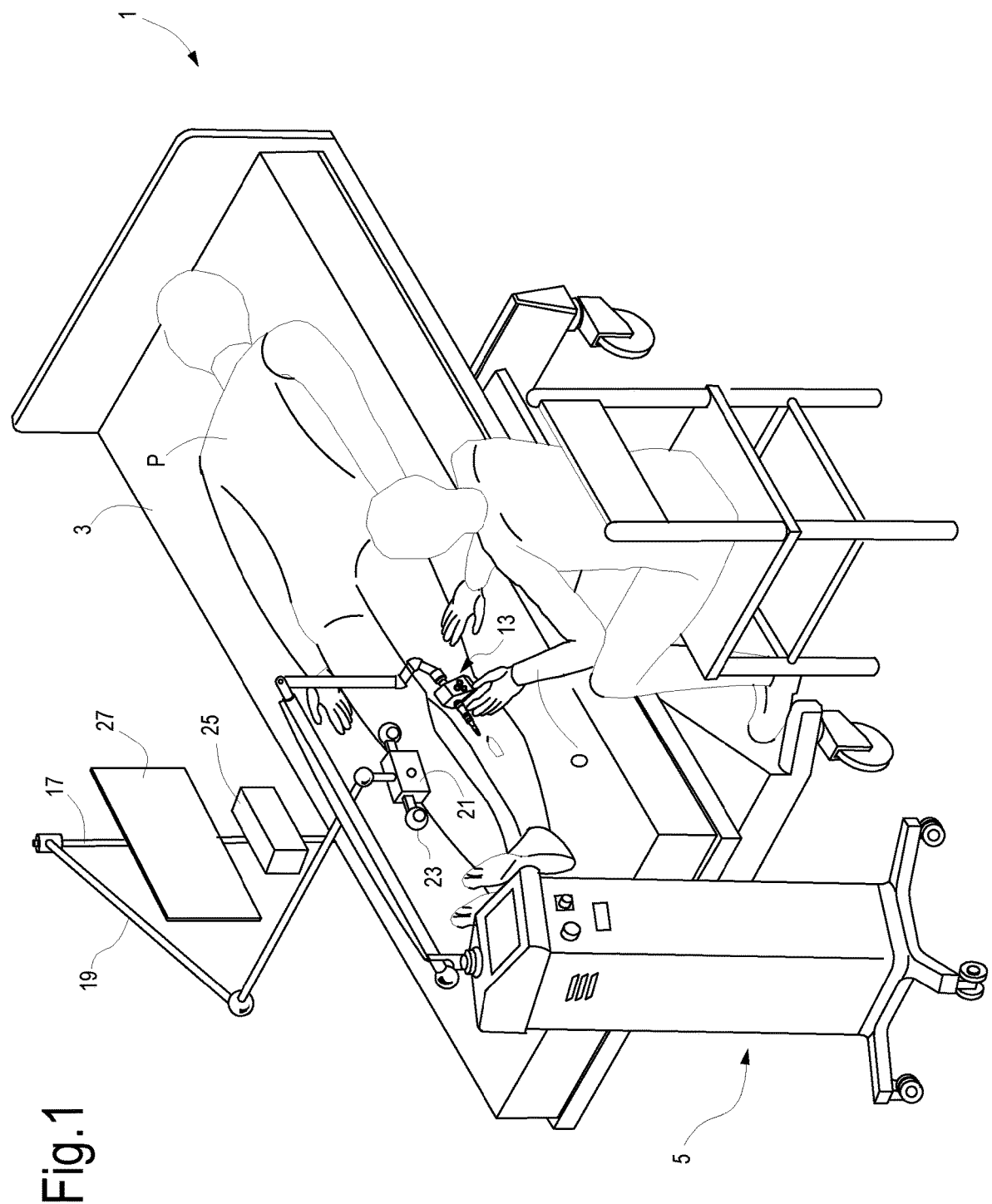
FIG. 1 schematically shows a surgical workplace for treating skin ulcers by means of the method disclosed herein.

FIG. 1 schematically shows a workplace 1 for treating skin ulcers through the method described herein. The workplace 1 may comprise an operating table 3, onto which the patient P lies. Number 5 indicates an equipment shown in greater detail in FIG. 2. The equipment 5 comprises a laser source 7 (see FIG. 2) arranged in a housing 9. Number 11 indicates a light guide adapted to convey a laser radiation from the laser source 7 to a hand-piece 13, also shown in the enlargement of FIG. 3. The light guide 11 may comprise, in a known manner, a plurality of tubes connected together by means of joints where mirrors are arranged for deviating the laser beam along the axis of each tube, so that the hand-piece 13 arranged at the distal end of the light guide 11 can be moved according to the needs of the operator O, the laser beam being always correctly transmitted between the source 7 and the hand-piece 13.

With reference to FIG. 2, number 13A indicates a main body of the hand-piece, where, for instance, scanning systems, lenses or other optical-electronic components may be arranged. The reference number 13B indicates the operational part of the hand-piece that can have a ferrule, for example a tip or an end element 15. Number 17 indicates, as a whole, interface or control elements, such as buttons or the like, allowing the operator to use the equipment 5.

The workplace 1 may also comprise a tripod or other support 17 that can be used to support a system for shooting and visualizing images. In the exemplary embodiment of FIG. 1, the support 17 comprises a preferably articulated arm 19 supporting a camera 21 and one or more lighting systems 23, for instance. The camera takes pictures of the operative field where the operator O is working with the hand-piece 13. The camera 21 may have an automatic focusing system.

The images taken by the camera 21 may be acquired by means of an image acquisition and processing system 25 supported by the support 17. The acquired and processed images may be stored and visualized on a screen, for instance a high resolution screen 27, supported by the support 17 and directed to allow easy visualization for the operator O.

The shooting system comprising the camera 21 may be a multi-spectral shooting system. The shooting system may be configured to shoot 3D images and therefore to further facilitate the tasks of the operator O.

Figure 4:
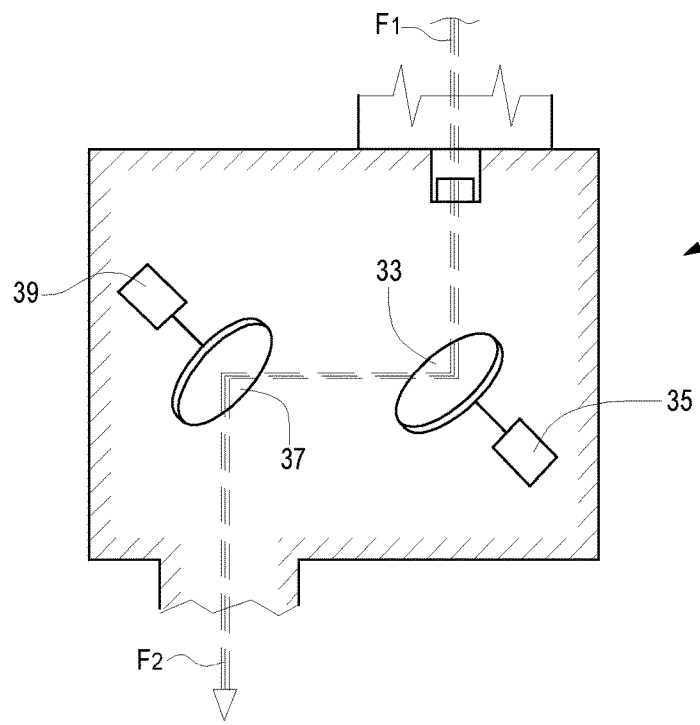
FIGS. 4, 5 and 6 show construction diagrams for lenses contained in the hand-piece of FIG. 3.

The hand-piece 13, the outside of which is schematically illustrated in FIGS. 2 and 3, may have a scanning system for the laser beam coming from the laser source 7 and guided by the light guide 11. FIG. 4 shows an embodiment of a scanning system 31, comprising a first scanning mirror 33 with a first actuator 35, for example a galvanometer, controlling the oscillation of the first mirror 33 around a first scanning axis. The scanning system 31 may comprise a second scanning mirror 37, associated with a second actuator 39, controlling the oscillation of the second scanning mirror 37 around a second scanning axis not parallel to the first scanning axis but usually orthogonal thereto.

In this way, the laser beam F1 entering the scanning system 31 can be moved according to a pattern that can be set on the equipment 5, so that the exiting laser beam F2 is controlled to impact on variable points of a target, i.e. of the ulcer to be treated.

In other embodiments, the scanning system 31 has a single scanning mirror and also a fixed mirror (with respect to the hand-piece 13) acting as deflection mirror. This configuration is illustrated by way of example in FIG. 5, where the single scanning mirror is indicated with 33 and the actuator thereof is indicated with 35, the actuator controlling small oscillations of the mirror 33 around at least two axes. Number 32 indicates a deflection mirror that is fixed with respect to the hand-piece 13.

Figure 5:
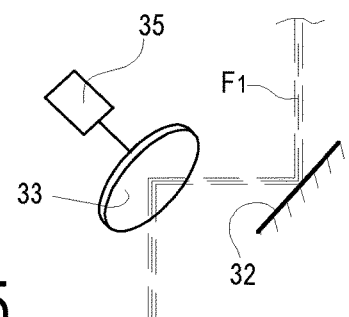

In some embodiments, the hand-piece 13 contains a collimation system usable for modifying the cross-section area of the laser beam F2 exiting from the hand-piece 13. In FIG. 5 a possible embodiment of the collimation system is schematically shown and labeled 41.

The collimation system 41 may comprise a first lens 43 and a second lens 45, coaxial with each other and movable with respect to each other according to arrow f41 in an axial direction, i.e. parallel to the coincident axes of the two lenses 43, 45. In some embodiments, the lens 43 is a converging lens, while the lens 45 is a diverging lens. By modifying the distance between the lenses 43, 45 it is possible to modify the cross-sectional area of the exiting beam F2 without changing the cross-sectional area of the entering beam F1.

In other embodiments, the collimation system 41 is arranged upstream of the scanning system 31 with respect to the propagation direction of the laser beam F1, F2.

In other embodiments, the collimation system is replaced by a focusing system through a converging lens, wherein the focal length can be selected and chosen by the operator. In some embodiments, lenses can also be provided suitable to generate, upon operator's control, a focused beam, wherein the focal length can be selected by the operator, or a collimated beam.

Even if in the attached figures the collimation system 41 is shown only in FIG. 5, it should be understood that a similar collimation system may be provided also for the scanning system 31 illustrated in FIG. 4.

The use of a collimation system allows having a collimated laser beam F2 exiting from the hand-piece, i.e. a beam with parallel rays. The beam may be directed towards the ulcer without the need of keeping the distance between the hand-piece 13 and the tissue surface, onto which the laser beam F2 impinges, constant. In fact, differently from what occurs when using a focusing system, in the case of a collimated beam the power density of the exiting beam F1 in the impinging area on the tissue is substantially unchanged with respect to the distance between the hand-piece 13 and the tissues, at least within sufficiently wide intervals with respect to the movements between hand-piece 13 and patient P, that are in the order of some centimeters.

Figure 6:
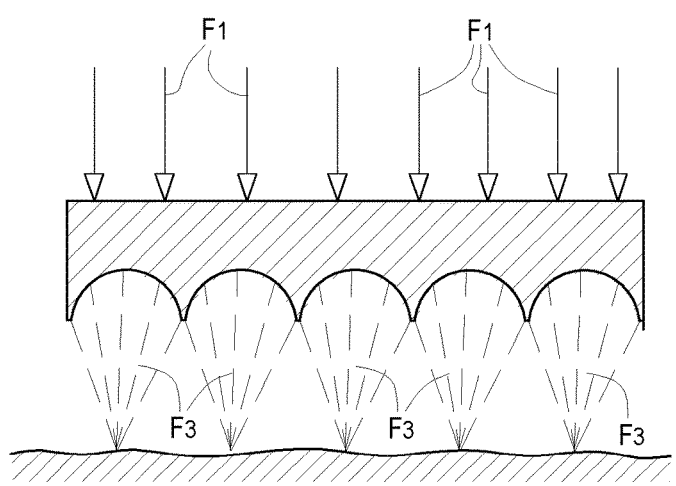

While with reference to FIGS. 4 and 5 a scanning system 31 has been illustrated allowing to move over the time the impinging point of the exiting laser beam F2 on the tissues, in other embodiments the hand-piece 13 comprises a lens subdividing an entering laser beam F1 into a plurality of adjacent beams F3, arranged according to a predetermined pattern. This solution is illustrated in FIG. 6; however it is less preferred, as on one hand it does not allow to modify the treatment pattern and, on the other hand, it does not allow to work with a collimated beam unless significantly complex lenses are used. Moreover, the multiple beams F3 are not suitable for tissue ablation as described below.

Figure 7:
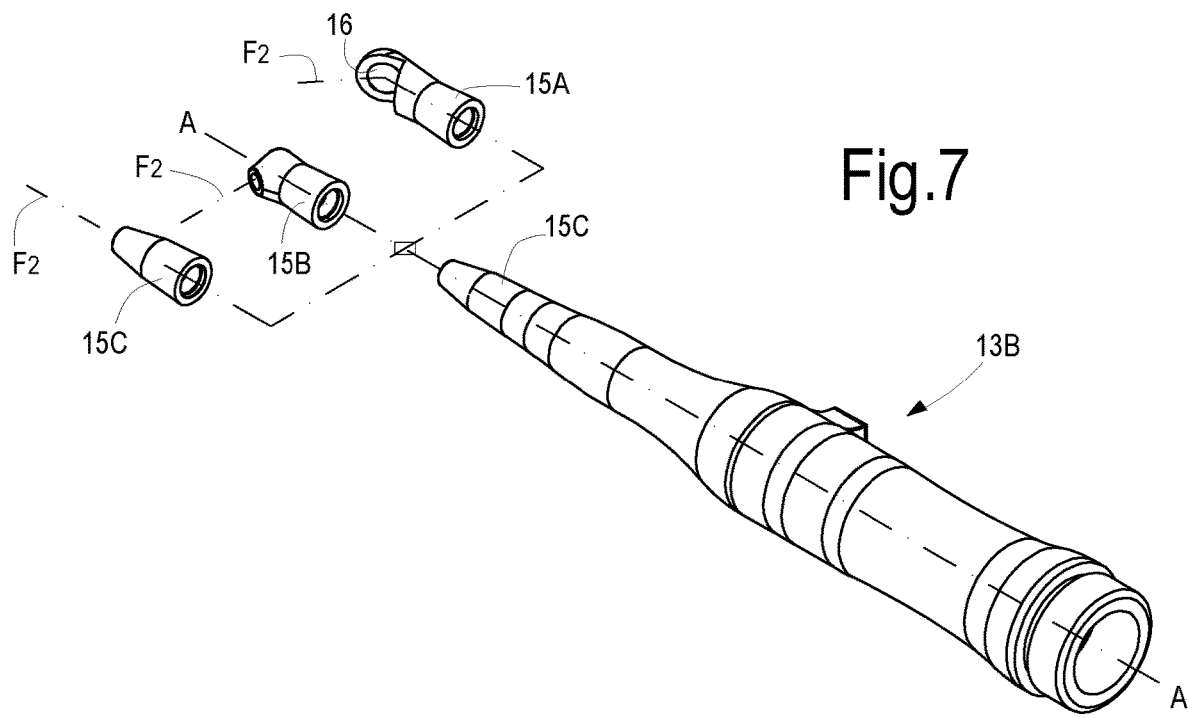
FIG. 7 shows an axonometric view of a hand-piece with interchangeable points for different working conditions.

FIG. 7 shows an axonometric view of the operational part 13B of an embodiment of a hand-piece 13. Said operational part may be applied in a removable manner. The hand-piece 13 may comprise a plurality of interchangeable end elements or ends, as schematically shown in FIG. 7, where three end elements 15A, 15B, 15C are shown, that can be alternatively mounted on the operational part 13B of the hand-piece 13.

The end elements 15A, 15B have deflection members, for example a deflection mirror 16 for the end element 15A and non-visible in the end element 15B. The deflection mirror deviates the exiting laser beam F2 so that it forms an angle, for instance a 90° angle, with the longitudinal axis A-A of the hand-piece 13.

Vice versa, the end element 15C is configured so that the exiting laser beam F2 is coaxial with the axis A-A of the hand-piece 13. The exit direction of the laser beam is represented with F2 for the three end elements 15A, 15B, 15C.

The use of end elements 15 that suitably deviate the exiting laser beam F2 allows particular advantages in treating ulcers, as it will be better explained below.

Even if in FIG. 7 only three different end elements 15A, 15B, 15C are shown, allowing two different orientations of the exiting laser beam F2 with respect to the axis A-A of the hand-piece 13, it is also possible to provide end elements 15 with differently arranged deflection elements, for instance mirrors or prisms, so that the exiting laser beam F2 is directed differently with respect to the axis A-A, for example forming an acute angle therewith.

A hand-piece 13 with interchangeable tips or end elements 15 (15A, 15B, 15C) is particularly advantageous from a construction and cost-saving viewpoint, as it has very simple structure, reduced weight and low cost. However, a similar hand-piece is not optimal in terms of flexibility and easiness of use.

Figure 8:
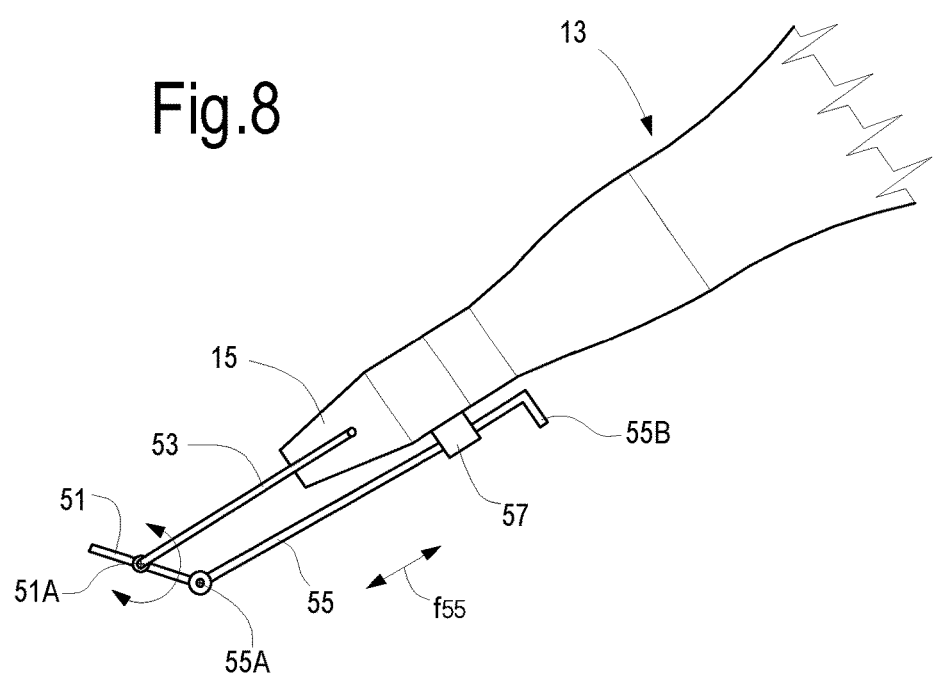
FIG. 8 shows a modified embodiment of a hand-piece particularly suitable for use in the treatment method according to the invention.

In some further embodiments the hand-piece 13 has an end element provided with a deflection mirror with adjustable inclination, so that it is possible, with only one element, to have exiting laser beams F2 with different inclinations with respect to the axis A-A of the hand-piece 13. This embodiment is shown in FIG. 8. In this case, a deflection mirror 51 is provided, that can be fastened to an end element 15 by means of a spacer 53. The deflection mirror 51 may be pivoted to the spacer 53 around an axis 51A orthogonal to the plane of FIG. 8. Any mechanism may be used to modify the inclination of the mirror 51 around the axis 51A. For example, in the embodiment of FIG. 8 a stem 55 is provided to this end, which is pivoted to the mirror 51 in 55A. In the embodiment of FIG. 8, the stem 55 is guided in a sleeve 57 where a friction material is contained, allowing the stem 55 to slide in the sleeve 57 applying force on an end appendix 55B of the stem 55, however keeping the stem 55 in stable position when no force is applied thereon, so that the angular position of the mirror 51 is kept unchanged.

The force on the stem 55 may be applied manually. In other embodiments, the force on the stem 55 may be applied by means of an actuator, which is controlled by a control unit of the equipment 3, for instance. The actuator, schematically shown in broken line and indicated with 56 in FIG. 10, may be an electronically controlled electric actuator.

Figure 9:
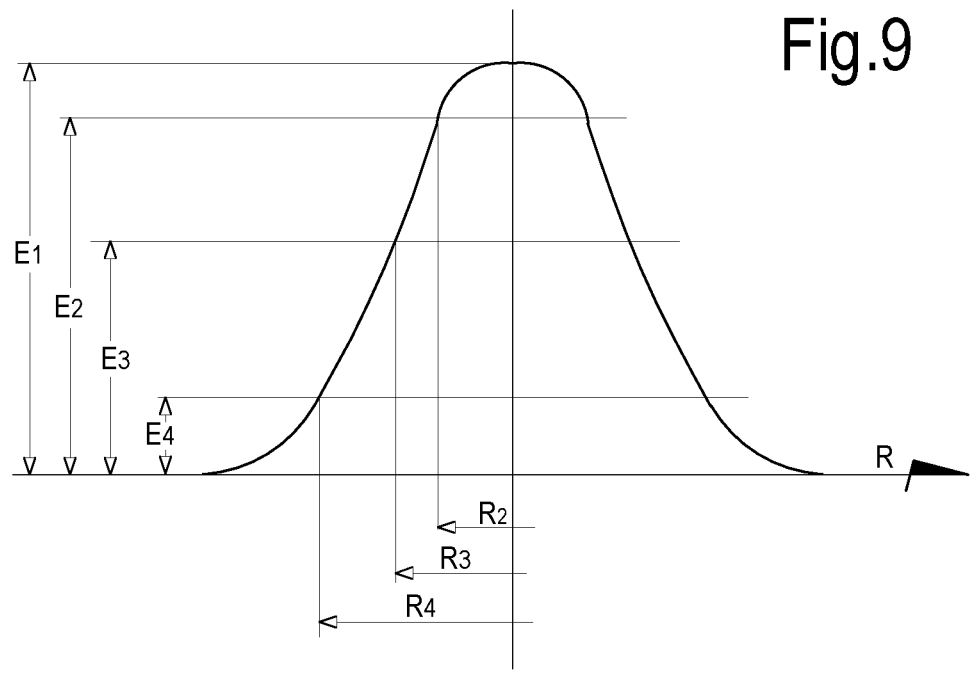
FIG. 9 shows a diagram of a possible power density distribution in a cross-section of a laser beam.

In some embodiments, the laser beam generated by the source 7 has advantageously a Gaussian power distribution, wherein the power density is maximal in the center and decreases towards the periphery of the beam cross-section (FIG. 9.) In some embodiments, to obtain a Gaussian beam the laser source cavity is designed so as to insulate the main propagation mode, and the focusing lenses are designed to contribute to maintaining the Gaussian shape of the power distribution from the axis towards the outside. By suitably choosing the cavity diameter and the radius of the mirrors of the source, it is possible to have a TEM00 oscillation mode, i.e. a Gaussian laser beam profile.

In FIG. 9 the laser beam has round cross-section, and three radii R2, R3, R4 (i.e. three distances from the beam axis) are indicated, to which three distinct power density values E2, E3, E4 correspond. E1 indicates the maximal power density, on the axis of the laser beam.

Through the hand-piece 13 a method is carried out for treating ulcer wounds, i.e. skin ulcers, that can be diabetes-linked. As mentioned above, in advantageous embodiments the method provides for a first operational step of so-called debridement, i.e. cleaning (also called escharotomy), during which the necrotic tissues and other debris are removed from the ulcer, reducing the bacterial load thereof, up to achieve sterile conditions, if possible. According to some embodiments of the inventive method, the debridement step is carried out through the laser beam generated by the source 7 and conveyed by means of the hand-piece 13 towards the skin ulcer. Debridement can also expose a portion of bone tissue under the skin ulcer to be treated. If the bone tissue has been attacked by necrosis, the necrotic part shall be removed through the laser beam during the debridement step or escharotomy.

Advantageously, the ulcer is cleaned by suitably adjusting the parameters of the laser beam generated by the source 7, so that the laser beam F2 has a vaporization or ablation effect on the tissues where it impacts. The wavelength of the laser emitted by the source 7 may be comprised, for example, between 500 nm and 13,000 nm, preferably between 9,000 nm and 11,000 nm, more preferably equal to 10,600 nm, this wavelength being generated by a $CO_2$ laser source.

In the debridement step, a pulsed laser radiation may be used. In some embodiments, the parameters usable in this step are as follows:
Average power: 0.1-80 W
Emission mode: continuous or, preferably, pulsed
Pulse duration (in case of pulsed emission): 0.5 µs-86 ms
Frequency (in case of pulsed emission): 5-200 Hz
Energy per pulse (in case of pulsed emission): 1.5 mJ-3 J
Exposition mode: continuous and timed
Spot diameter (i.e. diameter of the laser beam cross-section in the point where it impacts the tissues): from 150 micrometers up to 2,800 micrometers During the performed experiments and clinical treatments, the operators have often selected for the debridement, mainly during the self-learning steps, pulses with duration within 1 ms and average power comprised between 1 and 8 W.

Figure 10:
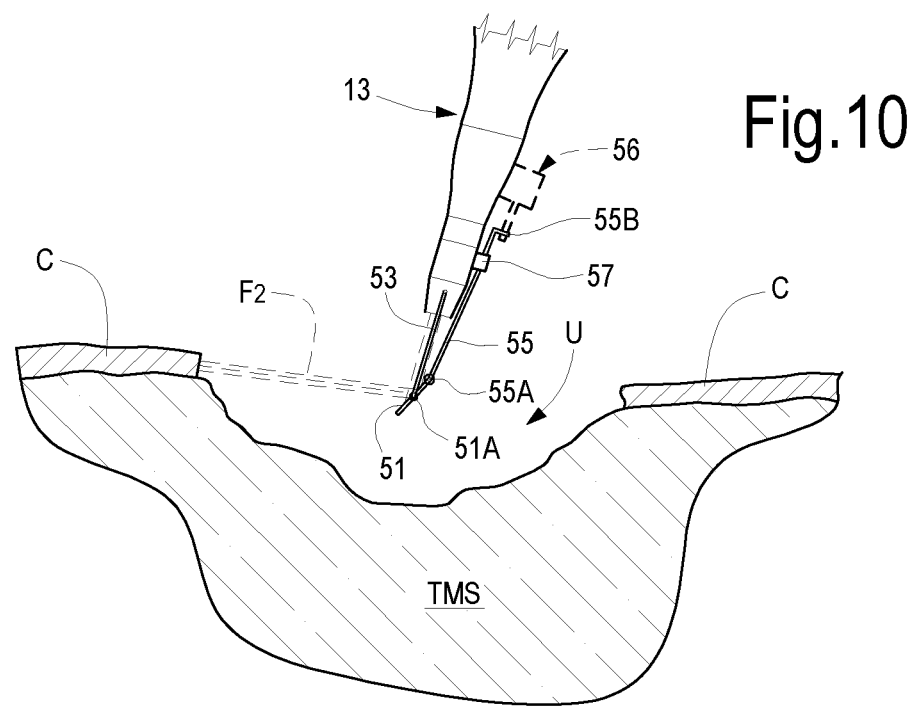
FIGS. 10-12 show different conditions of use of a hand-piece according to FIG. 8.
Figure 11:
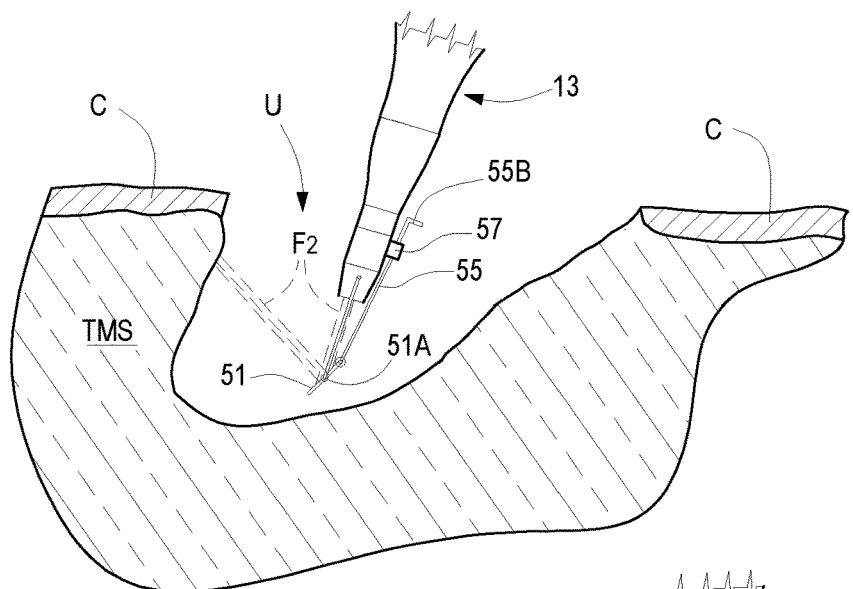
Figure 12:
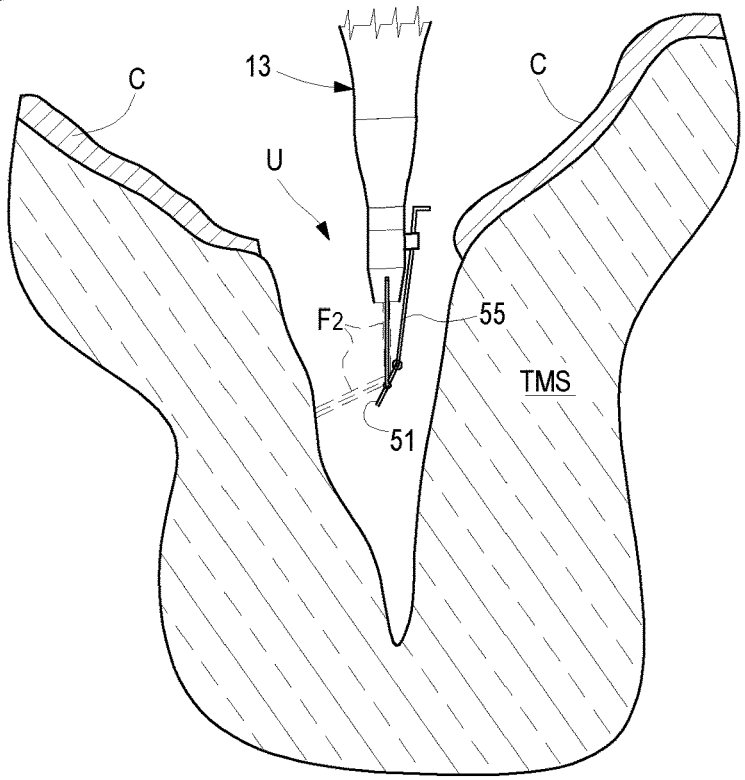

Skin ulcers may have particularly complex conformations and require to operate deeply in the soft tissues, in some cases up to achieve the bone tissue below. In order to facilitate cleaning or debridement it is advantageous to provide a hand-piece configured in one of the ways described above. FIGS. 10 to 12 show three different operational conditions that may occur in this step, treated with a hand-piece 13 of the type illustrated in FIG. 8. The figures are schematic and given just by way of example and have the only function of illustrating the modes of use and the advantages of this type of hand-piece.

Figure 13:
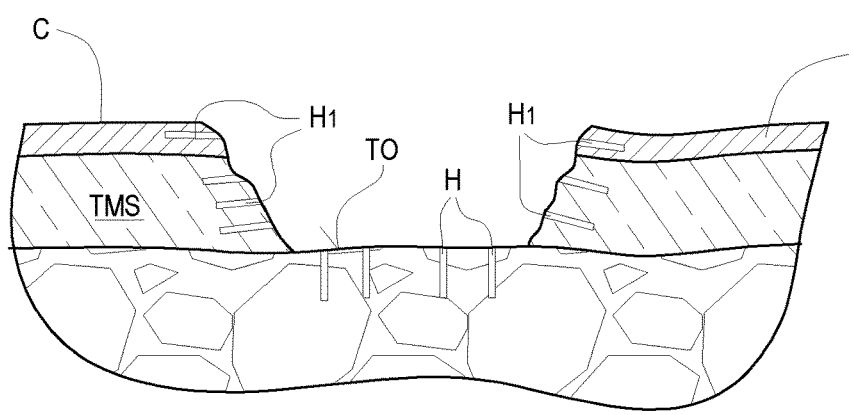
FIG. 13 schematically shows a treatment for bone tissue and soft tissue, with holes made through the laser beam.

In FIGS. 10 to 12, the letter U generically indicates the skin ulcer to be treated, C indicates the skin and TMS generically indicates subcutaneous soft tissues. In FIG. 13, also a portion of bone tissue TO is indicated.

In the condition shown in FIG. 10, through the hand-piece 13 a laser beam F2 is directed towards an edge of the ulcer U, more exactly in correspondence of the skin C. The deflection mirror 51 may be approximately at 45° with respect to the axis A-A of the hand-piece 13. The inclination angle between the axis A-A and the mirror actually depends on the habits of the operator O, who may keep the hand-piece 13 not orthogonal to the surface where the ulcer U is localized; in this case the inclination angle between axis A-A and deflection mirror 51 will be different than 45°.

In the operational condition shown in FIG. 11, the laser beam F2 is oriented so as to treat an undercut area of the ulcer. In the example of FIG. 11, subcutaneous soft tissue TMS is treated, but a similar orientation of the deflection mirror S may be useful also to treat skin C or bone tissue TO.

In the condition shown in FIG. 12, a deep ulcer is treated. In this case again, just by way of example, subcutaneous soft tissue TMS is treated, but it is also possible to treat bone tissue TO if the ulcer is so deep to affect also the bone tissue.

Escharotomy or debridement may be performed by manually moving the hand-piece 13 and keeping fixed the scanning mirrors contained therein, if any. In other embodiments, the movement of the scanning mirrors may be used to "spread" the laser beam on wider tissue areas keeping the hand-piece 13 in a fixed position or repositioning it manually to treat adjacent or not adjacent tissue portions.

Ulcer cleaning may be significantly facilitated by using the image acquisition system through the camera 21. In fact, visualizing the images of the operative field on a high-resolution screen 27 facilitates the task of the operator O and makes the intervention more efficient.

As mentioned above, in some cases the debridement step could expose at least a portion of healthy bone tissue. In the situation schematically shown in FIG. 13, the ulcer U has been cleaned and a cleaned surface portion of bone tissue TO has been exposed in the ulcer bed, cleaned and sterilized by means of the laser beam F1.

Once the ulcer has been cleaned, through the beam generated by the laser source 7, the second step of the method described herein is performed; this step comprises, for example in case of wounds that affect the bone tissue and could lead to amputation, the step of making small diameter holes in the cleaned bone tissue TO by means of the laser beam F2. FIG. 13 shows, just by way of example, holes H extending from the exposed surface of the bone tissue TO towards the inside thereof, if necessary up to the bone marrow. The holes may be very close to one another, and done according to a preset pattern. To this end, in some embodiments it is possible, keeping the hand-piece 13 in a fixed position, to make a plurality of holes H spaced from one another and distributed according to a suitable pattern, using the scanning system 31 described above and, in some situations, manually.

For example, the holes H may be arranged at a reciprocal distance comprised between 50 micrometers and 6,000 micrometers and preferably between 90 micrometers and 4,000 micrometers.

The diameter of the holes H may be comprised, for example, between 0.15 mm and 0.70 mm.

The depth of the holes H may typically vary according to the thickness of the wall separating the exposed surface of the bone tissue TO from the bone marrow contained therein and may be comprised, for example, between 90 micrometers and 4,000 micrometers.

The holes H made in the bone tissue cause blood to flow from the inside thereof. The blood contains a high number of pluripotent stem cells and cytokines, as well as growth factors, such as PDGF, TGF-$\beta$, IGF, VEGF, EGF, etc. These proteins are able to stimulate tissue regeneration and neo-angiogenesis, as well as cell proliferation and differentiation. Therefore, the stem cells appearing on the surface of the ulcer bed through the holes H are stimulated to proliferate and differentiate, surprisingly resulting in a tissue regeneration process, wherein the stem cells specialize and differentiate into cells of the various tissues facing the ulcer (bone tissue, soft tissue and skin).

The holes H in the bone tissue TO may be done with the same laser source used for ulcer debridement, with the same wavelength. Preferably, also for holing the bone tissue a pulsed laser beam is used, like in the debridement step. Typically, to make the holes H the following parameters are used (the values are given just by way of non-limiting example).

Average power: 0.1-80 W
Emission mode: continuous or, preferably, pulsed
Pulse duration (in case of pulsed emission): 0.5 $\mu$s-86 ms
Frequency (in case of pulsed emission): 5-200 Hz
Energy per pulse (in case of pulsed emission): 1.5 mJ-3 J
Exposition mode: continuous and timed
Spot diameter: from 150 micrometers to 700 micrometers Very satisfactory performances have been recorded during clinical treatments, both in terms of efficiency and low pain, making holes in the bone tissue according to the following parameters: average power about 80 W, pulse duration within 1 ms, exposition at least 50 ms.

According to further developments of the method described herein, in order to further facilitate tissue regeneration and to consequently accelerate ulcer healing, in some embodiments the laser beam is used to make holes, schematically indicated just by way of example with H1 in FIG. 13, also in subcutaneous soft tissues TMS and along the edges of the ulcer, in correspondence of the cutaneous tissue. Advantageously, the holes H1 are generated using the same hand-piece 13, with interchangeable end elements 15 or with a deflection mirror 51 with adjustable inclination. The same positions taken by the mirror 51 in FIGS. 10, 11, 12 and described above with reference to the debridement step may be also used to make the holes H1 in the tissues above the bone tissue TO.

The small holes H1 made in the soft tissues TMS and in the skin represent localized tissue damages, having the function of stimulating the organism reaction for the regenerative process. Practically, it has been found that the limited and targeted localized damages represented by the holes H1 stimulate the production of heat shock proteins and cause hyperthermia of the tissues surrounding the treated area. Hyperthermia causes a greater blood flow (hyperemia) and consequent supply of nutrients and growth hormones. Both these factors stimulate cell proliferation and differentiation, with a consequent acceleration of the regeneration processes. In other words, in the area where the blood flow is increased (hyperemia), this results in: an increase in temperature, a change in pH, NO and $O_2$ values, acceleration in cell differentiation and regeneration.

For making the holes H1, the same laser source 7 used for making the holes H can be used; however, it is also possible to use different laser sources for the various operations described herein (debridement, formation of holes H in the bone tissue and of holes H1 in the soft tissues and the skin).

The holes H1 may be arranged according to a pattern generated through laser scanning by using the scanning system 31 or, in some cases, manually, according to the features of the ulcer to be treated. The distance between holes H1 may be the same as between holes H. The depth of holes H1 may be comprised, for example, between 300 micrometers and 1,500 micrometers.

Also for making the holes H1 a pulsed beam can be used, as done for the holes H.

The laser parameters are advantageously selected so as to cause the desired localized damage, avoiding bleeding. To this end, the parameters shall be advantageously set to cause cauterization of the blood vessels intercepted by the laser beam during this step.

Typical parameters and values (given just by way of non-limiting example) for this step of the treatment method are as follows.

Average power: 0.1-80 W
Emission mode: continuous or, preferably, pulsed
Pulse duration (in case of pulsed emission): 0.5 µs-86 ms
Frequency (in case of pulsed emission): 5-200 Hz
Energy per pulse (in case of pulsed emission): 1.5 mJ-3 J
Exposition mode: continuous and timed
Spot diameter: between 120 micrometers and 700 micrometers Based on the clinical experiences done, often, in order to hole the soft tissue, the average power selected is comprised between 7 and 15 W, with pulse duration within 1 ms and exposition of at least 50 ms.

These parameters may be adjusted for example to regulate the treatment depth. The treatment depth can be adjusted by managing the laser intensity on the tissue, varying the pulse shape, the peak power, the average power emitted by the source, the spot dimension (i.e. the cross-sectional area of the beam), the time the beam is kept on the wound portion to be treated. The beam power density (that depends on the power emitted by the source and on the spot area) multiplied by the supply time in the same position gives the energy density deposited on the tissue and substantially determines the effect of ablation, vaporization of a given tissue thickness, cut for a given depth (in the debridement step), or bio-stimulation of a given tissue volume (in the subsequent step of bio-stimulating the tissue regeneration).

The method described above provides for the following steps: a debridement step up to expose a bone tissue portion, a step of perforating the bone tissue and a step of perforating the soft tissues. As mentioned above, the bone tissue perforation causes the exit of blood, which is rich in stem cells and growth factors, while the soft tissue perforation stimulates the regenerative processes.

According to the method described herein, it is also possible to omit the step of cleaning up to exposing the bone tissue. Namely, debridement can only provide for cleaning and sterilizing the ulcer, exposing only the soft tissues that are then perforated through the laser as described above in order to provide a localized damage and stimulate the regenerative processes. In this case, the bone tissue is not perforated.

It is also possible to clean the ulcer up to exposing the bone tissue, and then making holes only in the soft tissues, and not in the exposed bone tissue.

In less advantageous embodiments, the debridement step may be performed using classical methods instead of a laser beam, even if in this case the advantages are less the lower treatment efficiency is lower.

As it is clearly apparent from the description above, the treatment provides for various steps and may require different operative conditions. For example, in some cases it is useful to have a scanning system available, while in other cases a beam focusing system should be available with variable distance from the end of the hand-piece 13. In some cases it is useful to have available a system for automatically or manually varying the diameter of the laser beam or, more in general, the cross-sectional area thereof, while in some situations it is useful to have available a mirror able to deflect the exiting laser beam F2 according to angles variable based on the area to be treated and the shape and morphology thereof.

Even if, in the description above, embodiments have been described wherein the hand-piece is provided with different functions, for example with a scanning system, a system for varying the beam cross-section and a control system for controlling the deflection angle of the beam F2 exiting from the hand-piece 13, it is also possible to provide for a series of hand-pieces different in structure and function, each of which is provided with only one or more of the above mentioned functions. For instance, an equipment 3 of the type described above may be equipped with one or more of the following:

a hand-piece with a fixed beam exit angle (for instance axial exit, 90° angle, with or without interchangeable end element for modifying the exit angle by replacing the tip) and with no other controls, a hand-piece with fixed exit angle and system for adjusting the area of the beam cross-section;

a hand-piece with fixed exit angle and beam scanning system;

a hand-piece with fixed exit angle and variable focusing system;

a hand-piece with adjustable exit angle (deflection mirror with variable inclination) and with no other adjustments, a hand-piece with adjustable exit angle and system for adjusting the area of the beam cross-section;

a hand-piece with adjustable exit angle and beam scanning system;

a hand-piece with adjustable exit angle and variable focusing system.

Each of these hand-pieces has a simpler and lighter structure (that is therefore more practical) than a single hand-piece provided with more functions together. In some cases, a plurality of simple hand-pieces, interchangeable and usable in different treatment steps, could be preferred with respect to the use of a more complex, bulky and heavier hand-piece of less intuitive use.

Various aspects and embodiments of the methods disclosed herein are set forth in the following numbered clauses:

1. A method of skin ulcer treatment, comprising the steps of:
   escharotomy and debridement of the ulcer by removing soft tissues and, if necessary, up to expose bone tissue in the area of the treated ulcer;
   by means of a laser beam, forming a plurality of holes in the bone tissue in the ulcer area, said holes being deep enough to cause blood to flow from the inside of the bone tissue.

2. A method of skin ulcer treatment, comprising the steps of:
   escharotomy and debridement of the ulcer;
   making, by means of a laser beam, a plurality of holes in the soft tissues in the ulcer area, said holes forming micro-traumas for triggering physiological repairing mechanisms.

3. Method according to clause 1 or 2, wherein the step of escharotomy and debridement of the ulcer comprises the step of removing necrotic tissue by means of the laser beam.

4. Method according to clause 1, further comprising the step of forming, by means of the laser beam, a plurality of holes in the soft tissues near the ulcer edges after escharotomy and debridement.

5. Method according to one or more of the previous clauses, wherein the power density distribution of the laser beam varies between a central area and a peripheral area of the beam cross-section, the power density in the central area being greater than the power density in the peripheral area.

6. Method according to one or more of the previous clauses, wherein the power density distribution of the laser beam is Gaussian.

7. Method according to one or more of the previous clauses, wherein the step of making holes in the bone tissue comprises the step of forming said holes spaced from one another by a distance comprised between approximately 50 micrometers and approximately 6,000 micrometers, and preferably between approximately 90 micrometers and approximately 4,000 micrometers.

8. Method according to one or more of the previous clauses, wherein the step of forming holes in the bone tissue comprises a step of forming said holes with a diameter comprised between approximately 0.15 mm and approximately 0.70 mm.

9. Method according to one or more of the previous clauses, wherein the step of forming holes in the bone tissue comprises the step of forming said holes with a depth comprised between approximately 90 μm and approximately 4,000 μm.

10. Method according to one or more of the previous clauses, wherein the laser beam is a pulsed laser beam.

11. Method according to one or more of the previous clauses, wherein the wavelength of the laser beam is comprised between approximately 500 nm and approximately 13,000 nm, preferably between approximately 9,000 nm and approximately 11,000 nm, and more preferably equal to approximately 10,600 nm.

12. Method according to one or more of the previous clauses, wherein the holes in the bone tissue are made by means of a laser beam whose average power is comprised between approximately 0.1 W and approximately 80 W.

13. Method according to one or more of the previous clauses, wherein the holes in the bone tissue are formed by means of a pulsed laser beam whose peak power is preferably comprised between approximately 10 W and approximately 250 W, more preferably between approximately 40 W and approximately 190 W.

14. Method according to one or more of the previous clauses, wherein the holes formed in the soft tissues have a reciprocal distance comprised between approximately 50 micrometers and approximately 6,000 micrometers.

15. Method according to one or more of the previous clauses, wherein the holes formed in the soft tissues have a depth comprised between approximately 300 micrometers and approximately 1,500 micrometers.

16. Method according to one or more of the previous clauses, wherein the holes in the soft tissue are formed by means of a laser beam whose average power is comprised between approximately 7 W and approximately 15 W.

17. Method according to one or more of the previous clauses, wherein the holes in the soft tissue are formed by means of a pulsed laser.

18. Method according to one or more of the previous clauses, wherein the ulcer is cleaned by means of a laser beam with spot diameter comprised between approximately 150 micrometers and approximately 2,800 micrometers.

19. Method according to one or more of the previous clauses, wherein the holes in the bone tissue are formed by means of a laser beam with spot diameter comprised between approximately 150 micrometers and approximately 700 micrometers.

20. Method according to one or more of the previous clauses, wherein the holes in the soft tissues are formed by means of a laser beam with spot diameter comprised between approximately 120 micrometers and approximately 700 micrometers

The invention claimed is:

1. A method of skin ulcer treatment, comprising the steps of:
   escharotomy and debridement of an ulcer by removing soft tissues and expose bone tissue in an area of the ulcer;
   forming a plurality of holes in the bone tissue in an area of the ulcer via a laser beam, the holes being deep enough to cause blood to flow from inside of the bone tissue.

2. The method of claim 1, wherein the step of escharotomy and debridement of the ulcer comprises removing necrotic tissue via the laser beam.

3. The method of claim 1, further comprising the step of forming a plurality of holes in the soft tissues near ulcer edges after escharotomy and debridement.

4. The method of claim 1, wherein a power density distribution of the laser beam varies between a central area and a peripheral area of a beam cross-section, the power density in the central area being greater than the power density in the peripheral area.

5. The method of claim 1, wherein the step of making holes in the bone tissue comprises the step of forming the holes spaced from one another by a distance comprised between approximately 50 micrometers and approximately 6,000 micrometers.

6. The method of claim 1, wherein holes formed in the bone tissue have a reciprocal distance comprised between approximately 50 micrometers and approximately 6,000 micrometers.

7. The method of claim 1, wherein the step of making holes in the bone tissue comprises the step of forming the holes spaced from one another by a distance comprised between approximately 90 micrometers and approximately 4,000 micrometers.

8. The method of claim 1, wherein the step of forming holes in the bone tissue comprises a step of forming the holes with a diameter comprised between approximately 0.15 mm and approximately 0.70 mm.

9. The method of claim 1, wherein the step of forming holes in the bone tissue comprises the step of forming the holes with a depth comprised between approximately 90 μm and approximately 4,000 μm.

10. The method of claim 1, wherein the laser beam is a pulsed laser beam.

11. The method of claim 1, wherein the holes in the bone tissue are formed by a pulsed laser.

12. The method of claim 1, wherein a wavelength of the laser beam is comprised between approximately 500 nm and approximately 13,000 nm.

13. The method of claim 1, wherein a wavelength of the laser beam is comprised between approximately 9,000 nm and approximately 11,000 nm.

14. The method of claim 1, wherein a wavelength of the laser beam is equal to approximately 10,600 nm.

15. The method of claim 1, wherein the laser beam comprises an average power comprised between approximately 0.1 W and approximately 80 W.

16. The method of claim 1, wherein the holes in the bone tissue are formed by a pulsed laser beam whose peak power is comprised between approximately 10 W and approximately 250 W.

17. The method of claim 1, wherein the holes in the bone tissue are formed by a pulsed laser beam whose peak power is comprised between approximately 40 W and approximately 190 W.

18. The method of claim 1, wherein the holes formed in the bone tissue have a reciprocal distance comprised between approximately 50 micrometers and approximately 6,000 micrometers, wherein the holes formed in the bone tissue have a depth comprised between approximately 300 micrometers and approximately 1,500 micrometers.

19. The method of claim 1, wherein the holes formed in bone tissue have a reciprocal distance comprised between approximately 50 micrometers and approximately 6,000 micrometers, wherein the holes formed in the bone tissue have a depth comprised between approximately 300 micrometers and approximately 1,500 micrometers, wherein the holes in the bone tissue are formed by a laser beam whose average power is comprised between approximately 7 W and approximately 15 W.

20. The method of claim 1, wherein the ulcer is cleaned by a laser beam with spot diameter comprised between approximately 150 micrometers and approximately 2,800 micrometers.

21. The method of claim 1, wherein the holes in the bone tissue are formed by a laser beam with spot diameter comprised between approximately 120 micrometers and approximately 700 micrometers.

22. A method of skin ulcer treatment, comprising the steps of:

escharotomy and debridement of an ulcer by removing soft tissues and expose bone tissue in an area of the ulcer;

forming a plurality of holes in the bone tissue in the area of the ulcer via a laser beam, the holes being deep enough to cause blood to flow from inside of the bone tissue and causing bleeding of blood through the holes from an interior of the bone tissue in the area of the ulcer.

23. A method of skin ulcer treatment, comprising the steps of:

removing soft tissues and exposing bone tissue in an area of an ulcer;

forming a plurality of holes in the bone tissue via a laser beam such that blood flows from an interior of the bone tissue through the holes in the area of the ulcer.

\* \* \* \* \*